US010153311B2

(12) United States Patent
Adachi et al.

(10) Patent No.: US 10,153,311 B2
(45) Date of Patent: Dec. 11, 2018

(54) IMAGE SENSOR

(71) Applicant: OLYMPUS CORPORATION, Tokyo (JP)

(72) Inventors: Satoru Adachi, Tsuchiura (JP); Nana Akahane, Yamanashi (JP); Noriyuki Fujimori, Suwa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/668,807

(22) Filed: Aug. 4, 2017

(65) Prior Publication Data
US 2017/0330908 A1    Nov. 16, 2017

Related U.S. Application Data

(63) Continuation of application No. PCT/JP2015/075130, filed on Sep. 3, 2015.

(30) Foreign Application Priority Data

Feb. 10, 2015 (JP) ................................ 2015-024440

(51) Int. Cl.
*H01L 27/14* (2006.01)
*H01L 27/146* (2006.01)
(Continued)

(52) U.S. Cl.
CPC .......... *H01L 27/14609* (2013.01); *A61B 1/04* (2013.01); *A61B 1/051* (2013.01);
(Continued)

(58) Field of Classification Search
CPC ........................ H01L 27/14609; H01L 27/146
(Continued)

(56) References Cited

U.S. PATENT DOCUMENTS

| 5,555,520 A | 9/1996 | Sudo et al. |
| 9,627,432 B2 | 4/2017 | Kudoh |
(Continued)

FOREIGN PATENT DOCUMENTS

| JP | H03-272177 A | 12/1991 |
| JP | H04-101428 A | 4/1992 |
(Continued)

OTHER PUBLICATIONS

International Search Report dated Nov. 17, 2015 issued in PCT/JP2015/075130.

*Primary Examiner* — Jeffery A Williams
(74) *Attorney, Agent, or Firm* — Scully, Scott, Murphy & Presser, P.C.

(57) ABSTRACT

An image sensor includes: a pixel chip provided with a plurality of pixels, a plurality of first transfer lines, and a plurality of capacitors; a circuit chip provided with a plurality of column reading circuits, a plurality of column scanning circuits, a second transfer line, and a constant current source; and a connection portion stacked and provided between the pixel chip and the circuit chip and configured to connect a capacitor, which is arranged in the pixel chip and has a trench structure, and a first transistor arranged in the circuit chip to each other via an electrode. The capacitor is configured to form a transfer capacity removing a noise included in an imaging signal and connect the pixel chip and the circuit chip to each other via the electrode and the connection portion.

7 Claims, 11 Drawing Sheets

(51) Int. Cl.
*A61B 1/04* (2006.01)
*G02B 23/24* (2006.01)
*G02B 23/26* (2006.01)
*H04N 5/369* (2011.01)
*A61B 1/05* (2006.01)
*H01L 29/94* (2006.01)
*H04N 5/363* (2011.01)
*H04N 5/378* (2011.01)

(52) U.S. Cl.
CPC ............ *G02B 23/24* (2013.01); *G02B 23/26* (2013.01); *H01L 27/146* (2013.01); *H01L 27/1464* (2013.01); *H01L 27/14634* (2013.01); *H01L 27/14636* (2013.01); *H01L 29/945* (2013.01); *H04N 5/363* (2013.01); *H04N 5/369* (2013.01); *H04N 5/378* (2013.01); *H01L 27/14612* (2013.01); *H01L 27/14643* (2013.01)

(58) Field of Classification Search
USPC .......................................................... 348/65
See application file for complete search history.

(56) References Cited

U.S. PATENT DOCUMENTS

| | | |
|---|---|---|
| 2005/0224853 A1 | 10/2005 | Ohkawa |
| 2012/0056251 A1 | 3/2012 | Kudoh |
| 2014/0320618 A1* | 10/2014 | Akahane ................ H04N 5/363 |
| | | 348/65 |
| 2015/0179697 A1 | 6/2015 | Kudoh |

FOREIGN PATENT DOCUMENTS

| | | |
|---|---|---|
| JP | H07-161830 A | 6/1995 |
| JP | 2012-054495 A | 3/2012 |
| JP | 5140235 B2 | 2/2013 |
| JP | 2013-110254 A | 6/2013 |
| JP | 5596888 B1 | 9/2014 |

\* cited by examiner

IMAGE SENSOR

CROSS-REFERENCE TO RELATED APPLICATIONS

This application is a continuation of PCT international application Ser. No. PCT/JP2015/075130 filed on Sep. 3, 2015 which designates the United States, incorporated herein by reference, and which claims the benefit of priority from Japanese Patent Application No. 2015-024440, filed on Feb. 10, 2015, incorporated herein by reference.

BACKGROUND

1. Technical Field

The disclosure relates to an image sensor that generates image data of an object by capturing an image of the object.

2. Related Art

Hitherto, a technique is known in which only a transfer capacity for transferring an imaging signal is provided in a noise removing portion disposed in each of pixel columns in order to remove a reset noise of a charge voltage converting portion inside a unit pixel in a Complementary Metal Oxide Semiconductor (CMOS) image sensor (see JP 5596888 B1). According to this technique, it is possible to realize a compatibility between further miniaturization and high image quality of the image sensor by decreasing an area occupied by the noise removing portion while suppressing the capacity of the transfer capacity to be low without providing a sampling condenser inside the noise removing portion in terms of a noise signal reading operation of resetting the transfer capacity after resetting the pixel and outputting a signal of the pixel and an optical noise signal reading operation of outputting a signal of the pixel after transferring a charge stored in the pixel.

SUMMARY

In some embodiments, an image sensor includes: a pixel chip provided with a plurality of pixels, a plurality of first transfer lines, and a plurality of capacitors, the pixels being arranged in a two-dimensional matrix shape, each pixel being configured to receive external light, generate an imaging signal in response to a light receiving amount and output the generated imaging signal, the first transfer lines being configured to transfer the imaging signal output from each of the pixels, each first transfer line being provided for each vertical line in an arrangement of the pixels, each capacitor being provided at a respective one of the first transfer lines and having a trench structure including: a first diffusion layer connected to the first transfer line; a trench formed in the first diffusion layer; a dielectric film formed inside the trench; and an electrode provided inside the dielectric film; a circuit chip provided with a plurality of column reading circuits, a plurality of column scanning circuits, a second transfer line, and a constant current source, each column reading circuit including: a first transistor including a gate connected to the electrode, the first transistor being configured to amplify the imaging signal; and a second transistor including a source connected to the electrode, the second transistor being configured to reset the capacitor to a predetermined potential, each column reading circuit being provided at a respective one of the first transfer lines and separated from the capacitor by a second diffusion layer, each column scanning circuit including a third transistor connected to the first transfer line via the capacitor and configured to output the imaging signal from the first transfer line via the first transistor, each column scanning circuit being provided at a respective one of the column reading circuits, the second transfer line being connected to the third transistor and configured to transfer the imaging signal via the first transistor, the constant current source being connected to the second transfer line and configured to output the imaging signal from each of the first transfer lines to the second transfer line; and a connection portion stacked and provided between the pixel chip and the circuit chip and configured to connect the capacitor, which is arranged in the pixel chip and has the trench structure, and the first transistor arranged in the circuit chip to each other via the electrode. The capacitor is configured to form a transfer capacity removing a noise included in the imaging signal and connect the pixel chip and the circuit chip to each other via the electrode and the connection portion.

In some embodiments, an image sensor includes: a pixel chip provided with a plurality of pixels, a plurality of first transfer lines, and a plurality of capacitors, the pixels being arranged in a two-dimensional matrix shape, each pixel being configured to receive external light, generate an imaging signal in response to a light receiving amount and output the generated imaging signal, the first transfer lines being configured to transfer the imaging signal output from each of the pixels, each first transfer line being provided for each vertical line in an arrangement of the pixels, each capacitor being provided at a respective one of the first transfer lines and having a trench structure including: a first diffusion layer; a trench formed in the first diffusion layer; a dielectric film formed inside the trench; and an electrode provided inside the dielectric film and connected to the first transfer line; a circuit chip provided with a plurality of column reading circuits, a plurality of column scanning circuits, a second transfer line, and a constant current source, each column reading circuit including: a first transistor including a gate connected to the first diffusion layer, the first transistor being configured to amplify the imaging signal; and a second transistor including a source connected to the first diffusion layer, the second transistor being configured to reset the capacitor to a predetermined potential, each column reading circuit being provided at a respective one of the first transfer lines and separated from the capacitor by a second diffusion layer, each column scanning circuit including a third transistor connected to the first transfer line via the capacitor and configured to output the imaging signal from the first transfer line via the first transistor, each column scanning circuit being provided at a respective one of the column reading circuits, the second transfer line being connected to the third transistor and configured to transfer the imaging signal via the first transistor, the constant current source being connected to the second transfer line and configured to output the imaging signal from each of the first transfer lines to the second transfer line; and a connection portion stacked and provided between the pixel chip and the circuit chip and configured to connect the capacitor, which is arranged in the pixel chip and has the trench structure, and the first transistor arranged in the circuit chip to each other via the first diffusion layer. The capacitor is configured to form a transfer capacity removing a noise included in the imaging signal and connect the pixel chip and the circuit chip to each other via the first diffusion layer and the connection portion.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
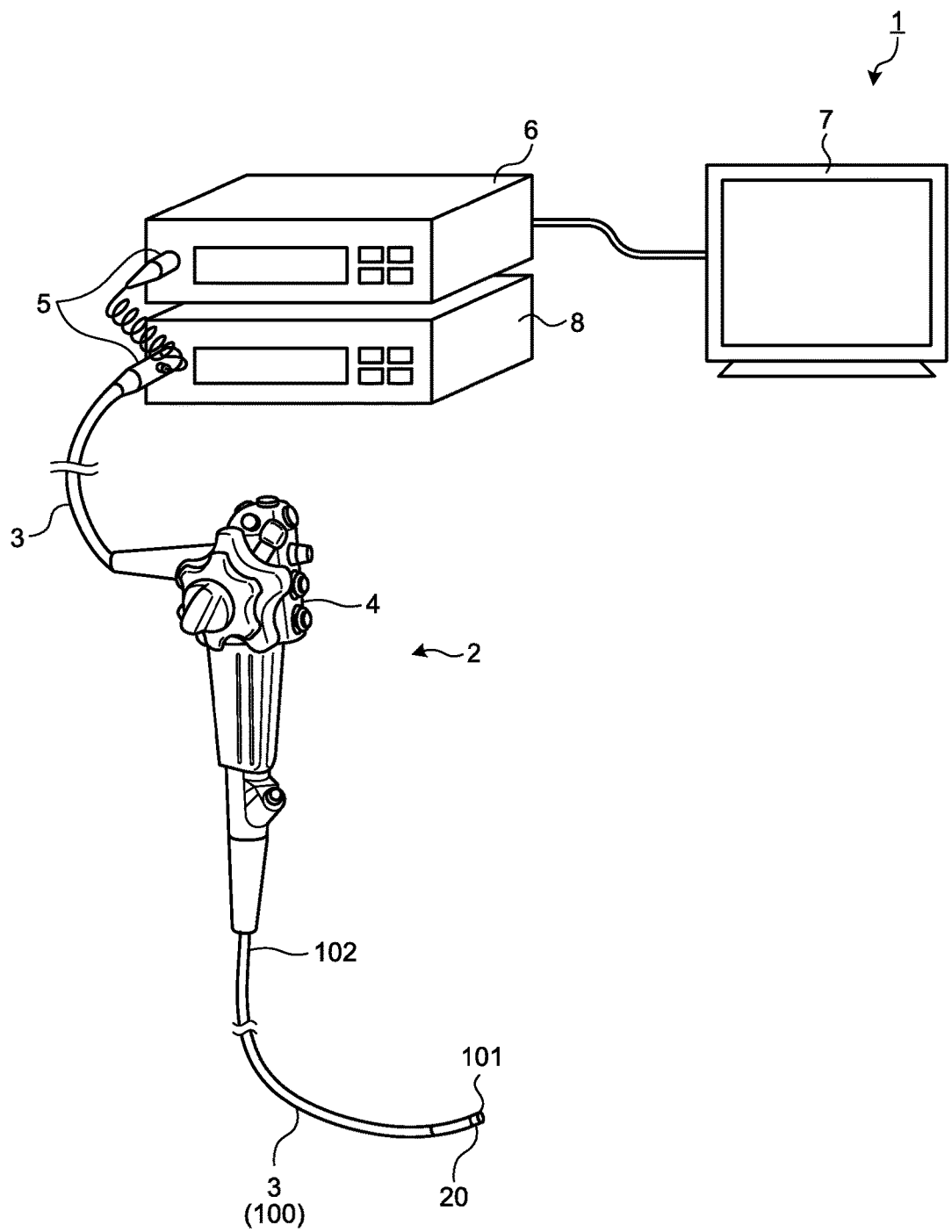
FIG. 1 is a diagram schematically illustrating an overall configuration of an endoscope system according to a first embodiment of the disclosure.

Hereinafter, an endoscope system including an imaging device will be described as a mode for carrying out the disclosure (hereinafter referred to as an "embodiment"). Further, the disclosure is not limited by the embodiment. Further, in the description of the drawings, the same parts will be described by the same reference numerals. Furthermore, it should be noted that the drawings are schematic and the relation between the thickness and the width of each member, the scale of each member, and the like are different from the reality. Also, parts having different dimensions and scales are included in the drawings.

First Embodiment

Configuration of Endoscope System

FIG. 1 is a diagram schematically illustrating an overall configuration of an endoscope system according to a first embodiment of the disclosure. An endoscope system 1 illustrated in FIG. 1 includes an endoscope 2, a transfer cable 3, a connector part 5, a processor 6 (a processing device), a display device 7, and a light source device 8.

The endoscope 2 captures an in-vivo image of a subject by inserting an insertion part 100 which is a part of the transfer cable 3 into a body cavity of the subject and outputs an image signal (image data) to the processor 6. Further, the endoscope 2 has a configuration in which an imaging unit 20 (an imaging device) for capturing an in-vivo image is provided at a position corresponding to one end side of the transfer cable 3 and corresponding to a distal end 101 of the insertion part 100 inserted into the body cavity of the subject and an operation part 4 for receiving various operations of the endoscope 2 is connected to a proximal end 102 of the insertion part 100. The imaging unit 20 is connected to the connector part 5 through the operation part 4 by the transfer cable 3. An image signal of an image which is captured by the imaging unit 20 is output to the connector part 5, for example, along the transfer cable 3 having a length of several meters.

The connector part 5 is connected to the endoscope 2, the processor 6, and the light source device 8 and performs a predetermined signal process on an image signal output from the connected endoscope 2 and a conversion (an A/D conversion) of converting an imaging signal from an analog signal into a digital signal so that the image signal is output to the processor 6.

The processor 6 includes a CPU (Central Processing Unit) and the like and is used to perform a predetermined image process on an image signal output from the connector part 5 and controls the entire endoscope system 1. Further, in the first embodiment, the processor 6 serves as a processing device.

The display device 7 displays an image corresponding to an image signal having been subjected to an image process of the processor 6. Further, the display device 7 displays various information on the endoscope system 1.

The light source device 8 includes, for example an xenon lamp or a white LED (Light Emitting Diode) and emits illumination light toward a subject from the distal end 101 of the insertion part 100 of the endoscope 2 via the connector part 5 and the transfer cable 3.

Figure 2:
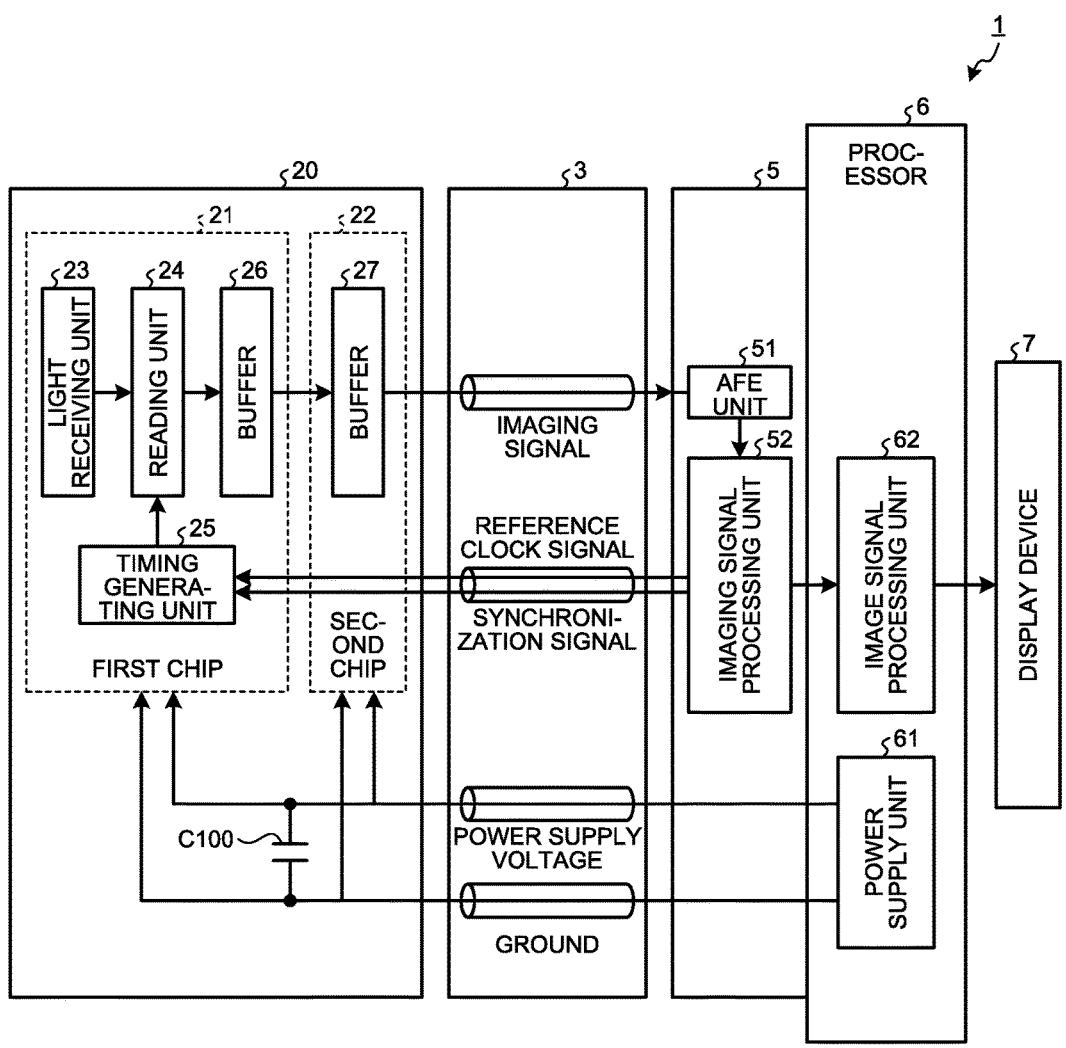
FIG. 2 is a block diagram illustrating a function of a main part of the endoscope system according to the first embodiment of the disclosure.

FIG. 2 is a block diagram illustrating a function of a main part of the endoscope system 1. Referring to FIG. 2, a detail of each configuration of the endoscope system 1 and a path of an electric signal inside the endoscope system 1 will be described.

As illustrated in FIG. 2, the imaging unit 20 includes a first chip 21 (an image sensor) and a second chip 22.

The first chip 21 includes a light receiving unit 23 in which a plurality of unit pixels are arranged in a matrix direction to have a two-dimensional matrix shape, a reading unit 24 which reads an imaging signal photoelectrically converted by the light receiving unit 23, a timing generating unit 25 which generates a timing signal based on a reference clock signal and a synchronization signal input from the connector part 5 and outputs the timing signal to the reading unit 24, and a buffer 26 which amplifies the imaging signal and the reference signal read from the light receiving unit 23 by the reading unit 24. In addition, a more detailed configuration of the first chip 21 will be described with reference to FIG. 3.

The second chip 22 includes a buffer 27 which serves as a transfer unit for transmitting the imaging signal output from the first chip 21 to the processor 6 via the transfer cable 3 and the connector part 5. In addition, a combination of circuits mounted on the first chip 21 and the second chip 22 can be appropriately changed in accordance with the setting.

Further, the imaging unit 20 receives a power supply voltage VDD which is generated by a power supply unit 61 inside the processor 6 via the transfer cable 3 together with a ground GND. A power stabilizing condenser C100 is provided between the ground GND and the power supply voltage VDD supplied to the imaging unit 20.

The connector part 5 includes an analog front end unit 51 (hereinafter, referred to as an "AFE unit 51") and an imaging signal processing unit 52. The connector part 5 serves as a relay processing part which electrically connects the endoscope 2 (the imaging unit 20) to the processor 6 and relays an electric signal. The connector part 5 and the imaging unit 20 are connected to each other via the transfer cable 3 and the connector part 5 and the processor 6 are connected to each other via a coil cable. Further, the connector part 5 is also connected to the light source device 8.

The AFE unit 51 receives an imaging signal transferred from the imaging unit 20, performs impedance matching using a passive element such as a resistor, extracts an AC component by a condenser, and determines an operation point by a voltage dividing resistor. The AFE unit 51 performs A/D converting on an analog imaging signal transferred from the imaging unit 20 and outputs a digital imaging signal to the imaging signal processing unit 52.

The imaging signal processing unit 52 performs a predetermined signal process such as vertical line removal and noise removal on the digital imaging signal input from the AFE unit 51 and outputs a result to the processor 6. The imaging signal processing unit 52 is configured by using, for example, a Field Programmable Gate Array (FPGA). Further, the imaging signal processing unit 52 generates a synchronization signal representing a start position of each frame based on a reference clock signal (for example, a clock signal of 27 MHz) supplied from the processor 6 and corresponding to a reference of an operation of each elements of the endoscope 2 and outputs the synchronization signal to the timing generating unit 25 of the imaging unit 20 via the transfer cable 3 along with the reference clock signal. Here, the synchronization signal includes a horizontal synchronization signal and a vertical synchronization signal.

The processor 6 is a control device which generally controls the entire endoscope system 1. The processor 6 includes a power supply unit 61 and an image signal processing unit 62.

The power supply unit 61 generates a power supply voltage VDD and supplies the generated power supply voltage to the imaging unit 20 via the connector part 5 and the transfer cable 3 along with the ground GND.

The image signal processing unit 62 performs an image process such as a synchronization process, a white balance (WB) adjustment process, a gain adjustment process, a gamma correction process, a digital/analog (for example, D/A) conversion process, and a format conversion process on the digital imaging signal having been subjected to the signal process by the imaging signal processing unit 52 to convert the imaging signal into an image signal and outputs the image signal to the display device 7.

The display device 7 displays an image captured by the imaging unit 20 based on the image signal input from the image signal processing unit 62. The display device 7 is configured by using a display panel such as a liquid crystal or an organic Electro Luminescence (EL).

Configuration of First Chip

Figure 3:
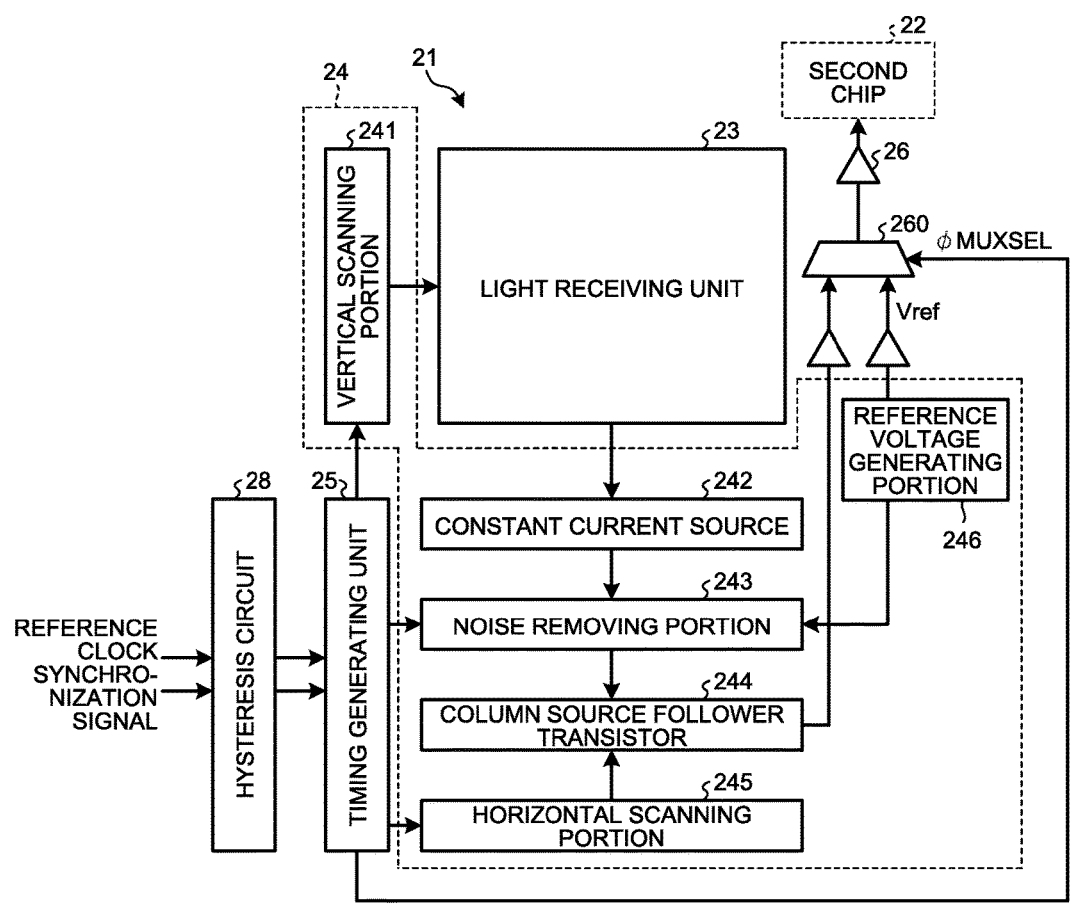
FIG. 3 is a block diagram illustrating a detailed configuration of a first chip illustrated in FIG. 2.
Figure 4:
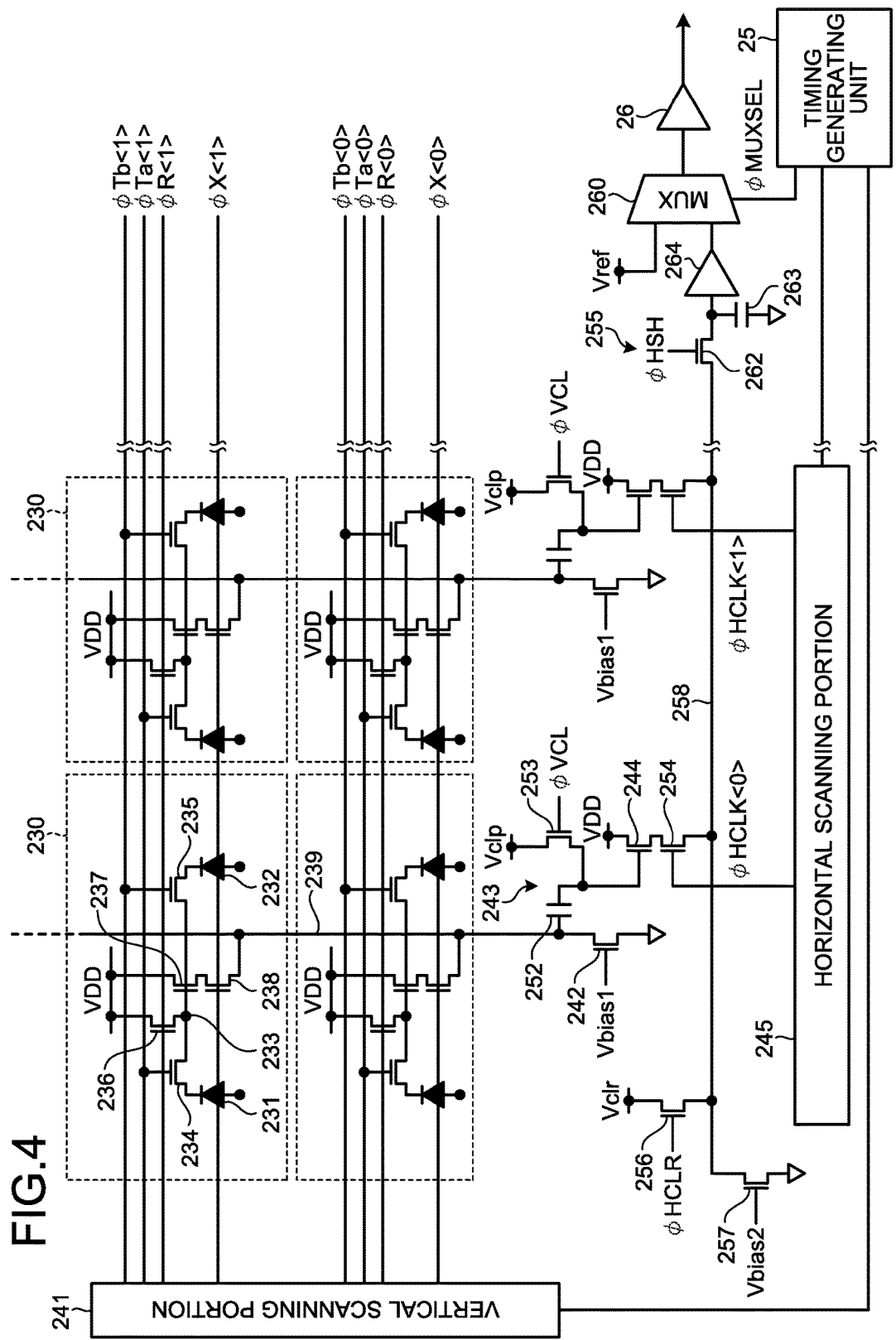
FIG. 4 is a circuit diagram illustrating a configuration of the first chip.

Next, a detailed configuration of the first chip 21 will be described. FIG. 3 is a block diagram illustrating a detailed configuration of the first chip 21 illustrated in FIG. 2. FIG. 4 is a circuit diagram illustrating a configuration of the first chip 21.

As illustrated in FIGS. 3 and 4, the first chip 21 includes the light receiving unit 23, the reading unit 24 (the driving unit), the timing generating unit 25, the buffer 26, and a hysteresis circuit 28.

The hysteresis circuit 28 performs waveform shaping on the reference clock signal and the synchronization signal input via the transfer cable 3 and outputs the reference clock signal and the synchronization signal having been subjected to the waveform shaping to the timing generating unit 25.

The timing generating unit 25 generates various drive signals (φTa, φTb, φR, φX, φVCL, φHCLR, φHCLK, φMUXSEL, φHSH) based on the reference clock signal and the synchronization signal shaped by the hysteresis circuit 28 and supplies the drive signals to a vertical scanning portion 241, a noise removing portion 243, a horizontal scanning portion 245, a multiplexer 260 (hereinafter, referred to as a "MUX 260"), and a reference voltage generating portion 246.

The reading unit 24 includes the vertical scanning portion 241 (the row selection circuit), a constant current source 242, the noise removing portion 243, a column source follower transistor 244 (a first transistor), a horizontal scanning portion 245 (a column selection circuit), and a reference voltage generating portion 246.

The vertical scanning portion 241 applies row selection signals φTa <N>, φTb <N>, φR<N>, and φX<N> to the selected rows <N> (N=0, 1, 2, . . . , n−1, n) of the light receiving unit 23 based on the drive signals (φT, φR, φX) supplied from the timing generating unit 25, drives unit pixels 230 of the light receiving unit 23 by the constant current source 242, transfers the imaging signal and the pixel resetting noise signal to a vertical transfer line 239, and outputs the signals to the noise removing portion 243.

The noise removing portion 243 removes an output variation and a pixel resetting noise signal of each unit pixel 230 and outputs an imaging signal photoelectrically converted by each unit pixel 230 to the column source follower transistor 244. In addition, a detail of the noise removing portion 243 will be described with reference to FIG. 4.

The horizontal scanning portion 245 applies a column selection signal φHCLK <M> to the selected columns <M> (M=0, 1, 2, . . . , m−1, m) of the light receiving unit 23 based on the drive signal (φHCLK) supplied from the timing generating unit 25, transfers the imaging signal photoelectrically converted by each unit pixel 230 to a horizontal transfer line 258 via the column source follower transistor 244, and outputs the imaging signal to the multiplexer 260.

The multiplexer 260 is driven by the drive signal (φMUXSEL) supplied from the timing generating unit 25 and alternatively outputs the imaging signal input via the horizontal transfer line 258 and the reference voltage Vref (the constant voltage signal) generated by the reference voltage generating portion 246 to the buffer 26. Here, the output reference voltage Vref is used in the imaging signal processing unit 52 and the like of the connector part 5 to remove the same-phase superimposed noise by the transfer cable 3 during the transfer of the imaging signal. Additionally, if necessary, an amplifier for adjusting a gain may be provided at the input side of the multiplexer 260.

The buffer 26 amplifies the noise removed imaging signal and the reference voltage Vref (the constant voltage signal) if necessary and alternately outputs the noise removed imaging signal and the reference voltage Vref to the second chip 22.

The plurality of unit pixels 230 are arranged in a two-dimensional matrix shape in the light receiving unit 23 of the first chip 21. Each unit pixel 230 includes a photoelectric conversion element 231 (a photodiode), a photoelectric conversion element 232, a charge conversion portion 233, a transfer transistor 234 (a first transfer portion), a transfer transistor 235, a charge conversion portion resetting portion 236 (a transistor), a pixel source follower transistor 237, and a pixel output switch 238 (a signal output portion). Further, in the specification, one or more photoelectric conversion elements and a transfer transistor for transferring a signal charge from the photoelectric conversion elements to the charge conversion portion 233 will be referred to as a unit cell. That is, the unit cell includes one or more photoelectric conversion elements and transfer transistors and each unit pixel 230 includes one unit cell.

The photoelectric conversion element 231 and the photoelectric conversion element 232 photoelectrically convert the incident light into a signal charge amount in response to the light amount and store the signal charge amount. Cathodes of the photoelectric conversion element 231 and the photoelectric conversion element 232 are respectively connected to one ends of the transfer transistor 234 and the transfer transistor 235 and anodes thereof are connected to the ground GND. The charge conversion portion 233 is configured as a floating diffusion capacity (FD) and converts a charge stored by the photoelectric conversion element 231 and the photoelectric conversion element 232 into a voltage.

The transfer transistor 234 and the transfer transistor 235 respectively transfer charges from the photoelectric conversion element 231 and the photoelectric conversion element 232 to the charge conversion portion 233. Signal lines to which row selection signals (row selection pulses) φTa and φTb are supplied are respectively connected to the gates of the transfer transistor 234 and the transfer transistor 235 and the charge conversion portion 233 is connected to the other end thereof. The transfer transistor 234 and the transfer transistor 235 are turned on when the row selection signals φTa and φTb are supplied from the vertical scanning portion 241 thereto via the signal line, signal charges are transferred from the photoelectric conversion element 231 and the photoelectric conversion element 232 to the charge conversion portion 233.

The charge conversion portion resetting portion 236 resets the charge conversion portion 233 to a predetermined potential. One end of the charge conversion portion resetting portion 236 is connected to the power supply voltage VDD, the other end thereof is connected to the charge conversion portion 233, and a gate thereof is connected to a signal line to which the row selection signal φR is supplied. The charge conversion portion resetting portion 236 is turned on when the row selection signal φR is supplied from the vertical scanning portion 241 thereto via the signal line and discharges the signal charge stored in the charge conversion portion 233 so that the charge conversion portion 233 is reset to a predetermined potential.

One end of the pixel source follower transistor 237 is connected to the power supply voltage VDD, the other end thereof is connected to one end of the pixel output switch 238, and a gate thereof receives a signal (an image signal or a resetting signal) converted into a voltage by the charge conversion portion 233.

The pixel output switch 238 outputs a signal which is converted into a voltage by the charge conversion portion 233 to the vertical transfer line 239. The other end of the pixel output switch 238 is connected to the vertical transfer line 239 and a gate thereof is connected to a signal line to which the row selection signal φX is supplied. The pixel output switch 238 is turned on when the row selection signal φX is supplied from the vertical scanning portion 241 to the gate of the pixel output switch 238 via the signal line and transfers the image signal or the resetting signal to the vertical transfer line 239.

The vertical transfer line 239 is provided for each vertical line of the unit pixel 230 and transfers the imaging signal output from the unit pixel 230.

The constant current source 242 is provided in each of the vertical transfer lines 239. One end of the constant current source 242 is connected to the vertical transfer line 239, the other end thereof is connected to the ground GND, and a gate thereof receives a bias voltage Vbias1. The constant current source 242 drives the unit pixel 230 and reads the output of the unit pixel 230 to the vertical transfer line 239. A signal which is read to the vertical transfer line 239 is input to the noise removing portion 243.

The noise removing portion 243 includes a transfer capacity 252 (a capacitor) and a clamp switch 253 (a second transistor).

One end of the transfer capacity 252 is connected to the vertical transfer line 239 and the other end thereof is connected to the column source follower transistor 244.

One end of the clamp switch 253 is connected to a signal line to which a clamp voltage Vclp is supplied from the reference voltage generating portion 246, the other end thereof is connected between the transfer capacity 252 and the column source follower transistor 244, and a gate thereof receives the drive signal φVCL from the timing generating unit 25. An imaging signal which is input to the noise removing portion 243 is an optical noise signal including a noise component.

When the drive signal φVCL is input from the timing generating unit 25 to the gate of the clamp switch 253, the clamp switch 253 is turned on so that the transfer capacity 252 is reset by the clamp voltage Vclp supplied from the reference voltage generating portion 246. The imaging signal having been subjected to noise removal by the noise removing portion 243 is input to the gate of the column source follower transistor 244.

Since the noise removing portion 243 does not need a sampling condenser (a sampling capacity), the capacity of the transfer capacity 252 (the AC coupling condenser) may be sufficiently larger than the input capacity of the column source follower transistor 244. In addition, it is possible to decrease the occupying area of the first chip 21 to a degree in which the noise removing portion 243 does not have a sampling capacity.

One end of the column source follower transistor 244 is connected to the power supply voltage VDD, the other end thereof is connected to one end of a column selection switch 254 (the third transistor), and a gate thereof receives an imaging signal having been subjected to noise removal by the noise removing portion 243. In addition, in the first embodiment, the column source follower transistor 244 (the first transistor) and the clamp switch 253 (the second transistor) serve as a column reading circuit.

One end of the column selection switch 254 is connected to the other end of the column source follower transistor 244, the other end thereof is connected to the horizontal transfer line 258 (the second transfer line), and a gate thereof is connected to a signal line which supplies the column selection signal φHCLK <M> from the horizontal scanning portion 245. The column selection switch 254 is turned on when the column selection signal φHCLK <M> is supplied from the horizontal scanning portion 245 to the gate of the column selection switch 254 of the column <M> and transfers a signal of the vertical transfer line 239 of the column <M> (an imaging signal having been subjected to noise removal of the noise removing portion 243) to the horizontal transfer line 258. Additionally, in the first embodiment, the column selection switch 254 serves as a column scanning circuit.

One end of a horizontal reset transistor 256 is connected to the ground GND, the other end thereof is connected to the horizontal transfer line 258, and a gate thereof receives the drive signal φHCLR from the timing generating unit 25. The horizontal reset transistor 256 is turned on when the drive signal φHCLR is input from the timing generating unit 25 to the gate of the horizontal reset transistor 256 and resets the horizontal transfer line 258.

One end of a constant current source 257 is connected to the horizontal transfer line 258, the other end thereof is connected to the ground GND, and a gate thereof receives a bias voltage Vbias2. The constant current source 257 reads an imaging signal from the vertical transfer line 239 to the horizontal transfer line 258. The imaging signal which is read to the horizontal transfer line 258 is input to a sample hold portion 255.

The horizontal transfer line 258 is connected to each of the column selection switches 254 and transfers an imaging signal via the column source follower transistor 244.

The sample hold portion 255 includes a sample hold switch 262 (a transistor), a sample capacity (a condenser) 263, and an op amp 264. One end of the sample hold switch 262 is connected to the horizontal transfer line 258, the other end thereof is connected to the input of the op amp 264, and an imaging signal and a horizontal resetting noise signal are input thereto via the horizontal transfer line 258. One end of the sample capacity 263 is connected to the other end of the sample hold switch 262 and the input of the op amp 264 and the other end thereof is connected to the ground GND. The output of the op amp 264 is connected to the inverting input terminal of the op amp 264 and the input of the multiplexer 260. The sample hold portion 255 holds a voltage immediately before the sample hold switch 262 is turned off by the sample capacity 263 and outputs a voltage held by the sample capacity 263 while the sample hold switch 262 is turned off.

In the first embodiment, it is possible to suppress the crosstalk of the imaging signal in the column direction by alternatively performing the resetting of the horizontal transfer line 258 using the horizontal reset transistor 256 and the reading of the imaging signal having been subjected to noise removal from the vertical transfer line 239. Further, when the sample hold switch 262 of the sample hold portion 255 is turned on during the transfer of the imaging signal having been subjected to the noise removal and is turned off during the transfer of the resetting noise signal, only the imaging signal having been subjected to noise removal can be output to the op amp 264. Since the first chip 21 includes the sample hold portion 255, the band of the amplifier circuit in the subsequent stage can be halved and the range thereof can be suppressed.

The multiplexer 260 alternatively outputs the noise removed imaging signal output from the sample hold portion 255 and the reference voltage Vref generated by the reference voltage generating portion 246 to the second chip 22.

In the second chip 22, only AC components of the noise removed imaging signal and the reference voltage Vref are transferred to the connector part 5 via the transfer cable 3.

Figure 5:
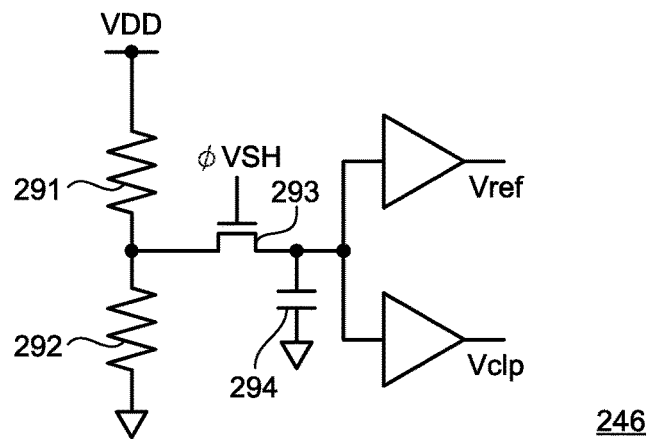
FIG. 5 is a circuit diagram illustrating a configuration of a reference voltage generating portion of a light receiving unit of the endoscope system according to the first embodiment of the disclosure.

FIG. 5 is a circuit diagram illustrating a configuration of the reference voltage generating portion 246 of the light receiving unit 23 of the endoscope system 1 according to the first embodiment. The reference voltage generating portion 246 (the constant voltage signal generating portion) includes a resistance voltage dividing circuit which includes two resistors 291 and 292 and a sampling capacity 294 (a condenser) which releases fluctuation independently from the power supply and the switch 293 (the transistor) driven by the drive signal φVSH. The reference voltage generating portion 246 generates the clamp voltage Vclp of the noise removing portion 243 and the reference voltage Vref (the constant voltage signal) from the same power supply voltage VDD as that of the light receiving unit 23 at a timing in which the drive signal φVSH is driven by the driving of the switch 293.

Since the reference voltage Vref and the clamp voltage Vclp are generated at the same timing from the same power supply, the reference voltage Vref reflects an influence of the power fluctuation for the imaging signal output from the noise removing portion 243. Further, the reference voltage Vref reflects the transfer noise information during transfer in the transfer cable 3. Thus, it is possible to obtain the imaging signal from which noise is removed during transfer by performing a noise removal process such as a correlated double sampling on the connector part 5 in such a manner that the noise removed imaging signal and the reference voltage Vref are alternatively transferred to the connector part 5.

Figure 6:
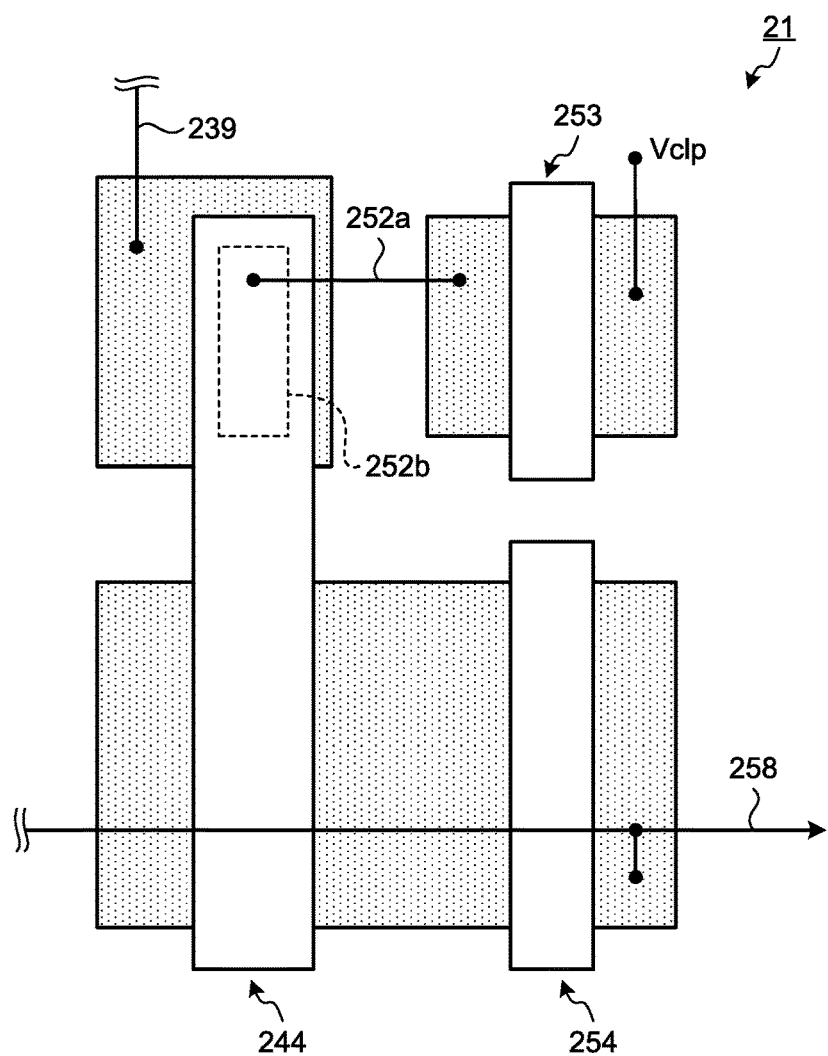
FIG. 6 is a top view of a first chip including at least a column source follower transistor, a transfer capacity, a clamp switch, and a column selection switch.
Figure 7:
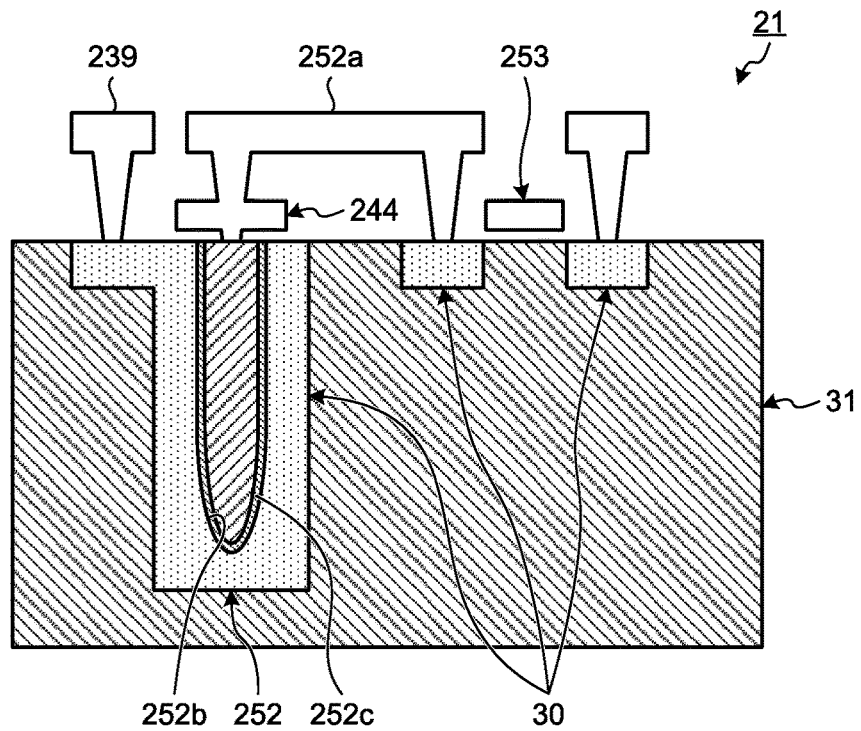
FIG. 7 is a cross-sectional view obtained by cutting a first chip at a position including at least a transfer capacity.

Next, the arrangement of the column source follower transistor 244, the transfer capacity 252, the clamp switch 253, and the column selection switch 254 will be described. FIG. 6 is a top view of the first chip 21 including at least the column source follower transistor 244, the transfer capacity 252, the clamp switch 253, and the column selection switch 254. FIG. 7 is a cross-sectional view obtained by cutting the first chip 21 at a position including at least the transfer capacity 252.

As illustrated in FIGS. 6 and 7, the transfer capacity 252 (the capacitor) has a trench structure including a first electrode 252a formed on a first diffusion layer 30. Further, the transfer capacity 252 includes a trench 252b which is formed in the first diffusion layer 30 and a dielectric film 252c which is formed inside the trench 252b. The dielectric film 252c is formed of $SiO_2$ (silicon oxide), $Si_3N_4$ (silicon nitride), $Al_2O_3$ (aluminum oxide), $HfO_2$ (hafnium oxide), $ZrO_2$ (zirconium oxide), $Ta_2O_5$ (tantalum oxide), $TiO_2$ (titanium oxide), $Y_2O_3$ (yttrium oxide), and $La_2O_3$ (lanthanum oxide). Further, the first electrode 252a is formed at the inside of the dielectric film 252c in the transfer capacity 252. Further, the vertical transfer line 239 is connected to the first diffusion layer 30. Accordingly, the imaging signal from the pixel output switch 238 is transferred to the first diffusion layer 30.

A gate of the column source follower transistor 244 (the first transistor) is connected to the first electrode 252a via the trench 252b, a drain thereof is connected to the power supply voltage VDD, and a source thereof is connected to the column selection switch 254 (the third transistor). The column source follower transistor 244 amplifies the imaging signal output from the pixel output switch 238 via the vertical transfer line 239 and outputs the imaging signal to the horizontal transfer line 258 via the column selection switch 254.

A source of the clamp switch 253 (the second transistor) is connected to the first electrode 252a via the trench 252b and a drain thereof is connected to a signal line from which the clamp voltage Vclp is supplied from the reference voltage generating portion 246. The clamp switch 253 is turned on when the drive signal φVCL is input thereto from the timing generating unit 25, resets the potential of the first electrode 252a inside the trench 252b to the clamp voltage Vclp supplied from the reference voltage generating portion 246, and transfers only the imaging signal output from the pixel output switch 238 via the vertical transfer line 239 to the column source follower transistor 244.

The column selection switch 254 (the third transistor) is connected to the vertical transfer line 239 via the transfer capacity 252 and outputs the imaging signal from the vertical transfer line 239 to the horizontal transfer line 258 via the column source follower transistor 244.

Further, each of the column reading circuit including the column source follower transistor 244 and the clamp switch 253 is separated by a second diffusion layer 31.

According to the above-described first embodiment of the disclosure, it is possible to realize a compatibility between further miniaturization and high image quality by forming the transfer capacity 252 in a trench structure.

First Modified Example of First Embodiment

Figure 8:
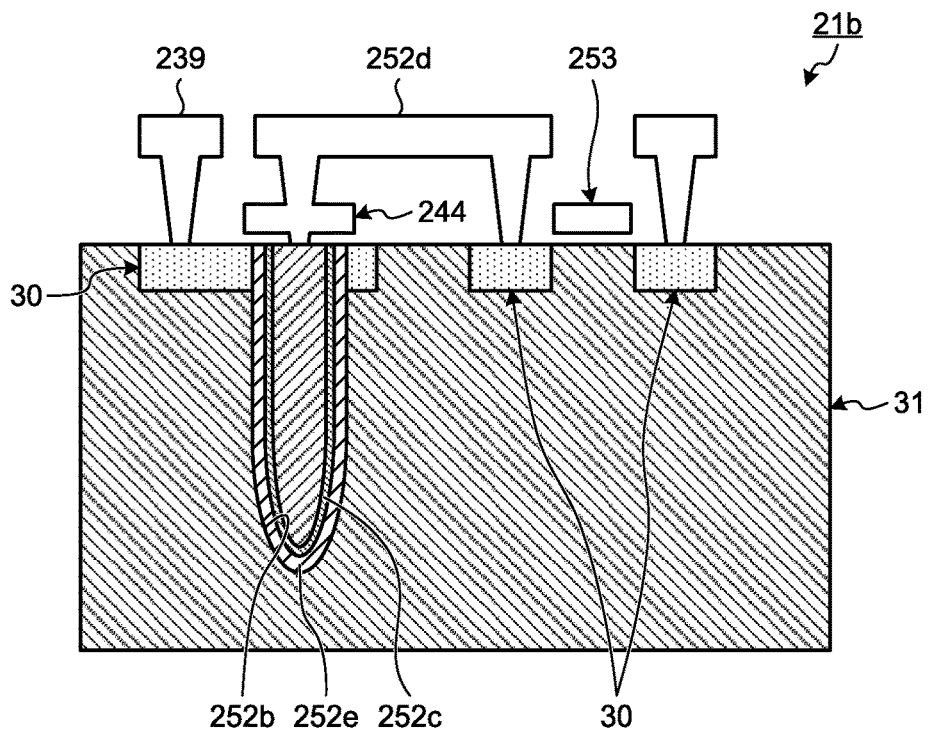
FIG. 8 is a cross-sectional view obtained by cutting a first chip at a position including a transfer capacity of a first modified example of the first embodiment of the disclosure.

Next, a first modified example of the first embodiment of the disclosure will be described. FIG. 8 is a cross-sectional view of a first chip obtained by cutting at a position including a transfer capacity of a first modified example of the first embodiment of the disclosure. In the first modified example of the first embodiment, the same reference numerals will be given to the same elements as those of the endoscope system 1 according to the above-described first embodiment and the description thereof will be omitted.

As illustrated in FIG. 8, a first chip 21b includes a first electrode 252d and a second electrode 252e instead of the first electrode 252a connected to the vertical transfer line 239 of the transfer capacity 252 according to the above-described first embodiment. The second electrode 252e is formed by using an impurity-doped polysilicon and is formed to be embedded in the trench 252b. The dielectric film 252c is formed inside the second electrode 252e. Further, the first electrode 252d is formed inside the dielectric film 252c. Furthermore, the first electrode 252d is formed at a position facing the second electrode 252e with the dielectric film 252c interposed therebetween. Further, the first diffusion layer 30 is connected to each of the second electrode 252e and the vertical transfer line 239.

According to the first modified example of the first embodiment of the disclosure, since the dielectric film 252c and the first electrode 252d are formed after the second electrode 252e is provided in the trench 252b formed on the second diffusion layer 31, it is possible to form a deep trench 252b without using a high-energy ion implanter.

Second Modified Example of First Embodiment

Figure 9:
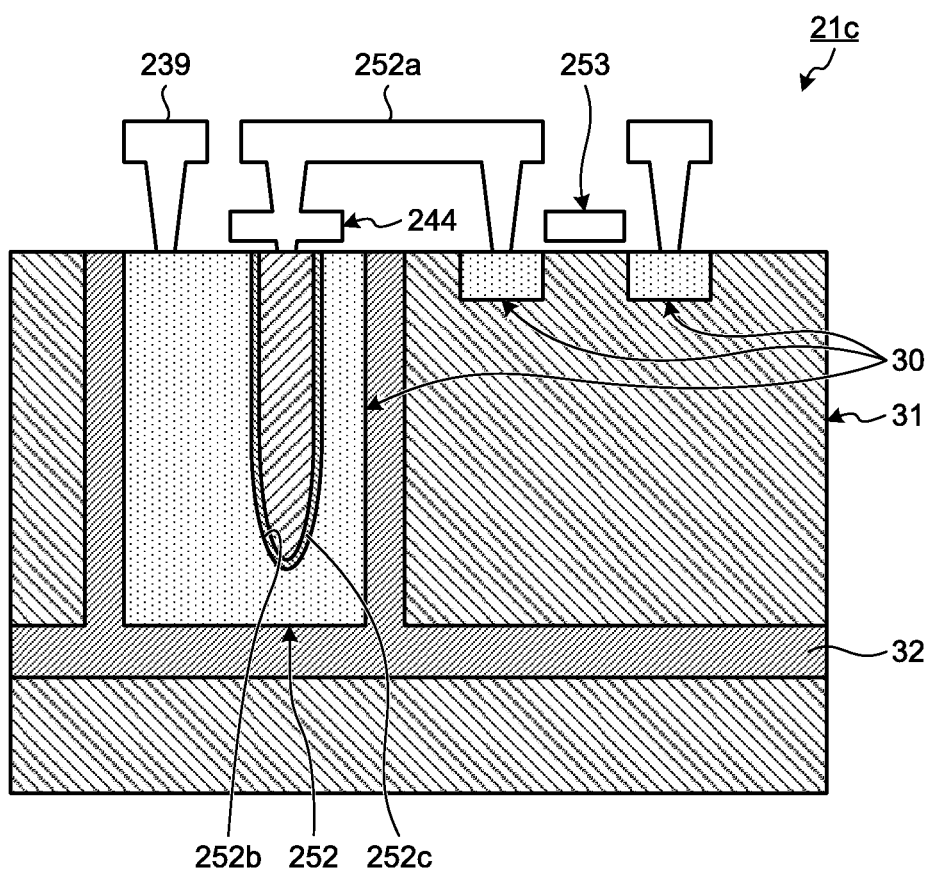
FIG. 9 is a cross-sectional view obtained by cutting a first chip at a position including a transfer capacity of a second modified example of the first embodiment of the disclosure.

Next, a second modified example of the first embodiment of the disclosure will be described. FIG. 9 is a cross-sectional view of a first chip obtained by cutting at a position including the transfer capacity of the second modified example of the first embodiment of the disclosure. Additionally, in the second modified example of the first embodiment, the same reference numerals will be given to the same elements as those of the endoscope system 1 according to the above-described first embodiment and the description thereof will be omitted.

A first chip 21c illustrated in FIG. 9 includes a separation member 32 that separates the first diffusion layer 30 and the second diffusion layer 31 from each other. Specifically, the first chip 21c is formed by using a Silicon On Insulator (SOI) substrate including a layer of a silicon oxide film, a deep trench deeper than the trench 252b is formed in the second diffusion layer 31, and the separation member 32 formed as a silicon oxide film is injected thereinto, thereby separating the first diffusion layer 30 and the second diffusion layer 31 from each other.

According to the second modified example of the above-described first embodiment, since the first diffusion layer 30 and the second diffusion layer 31 are separated from each other by the separation member 32, the capacity of the column source follower transistor 244 can be decreased.

Second Embodiment

Next, a second embodiment of the disclosure will be described. In the second embodiment, a configuration of a first chip is different from a configuration of the first chip 21 according to the above-described first embodiment. Specifically, a stacked imager chip will be used as the first chip according to the second embodiment. For this reason, a configuration of the first chip according to the second embodiment will be described here below. In addition, the same reference numerals will be given to the same elements as those of the endoscope system 1 according to the above-described first embodiment and the description thereof will be omitted.

Figure 10:
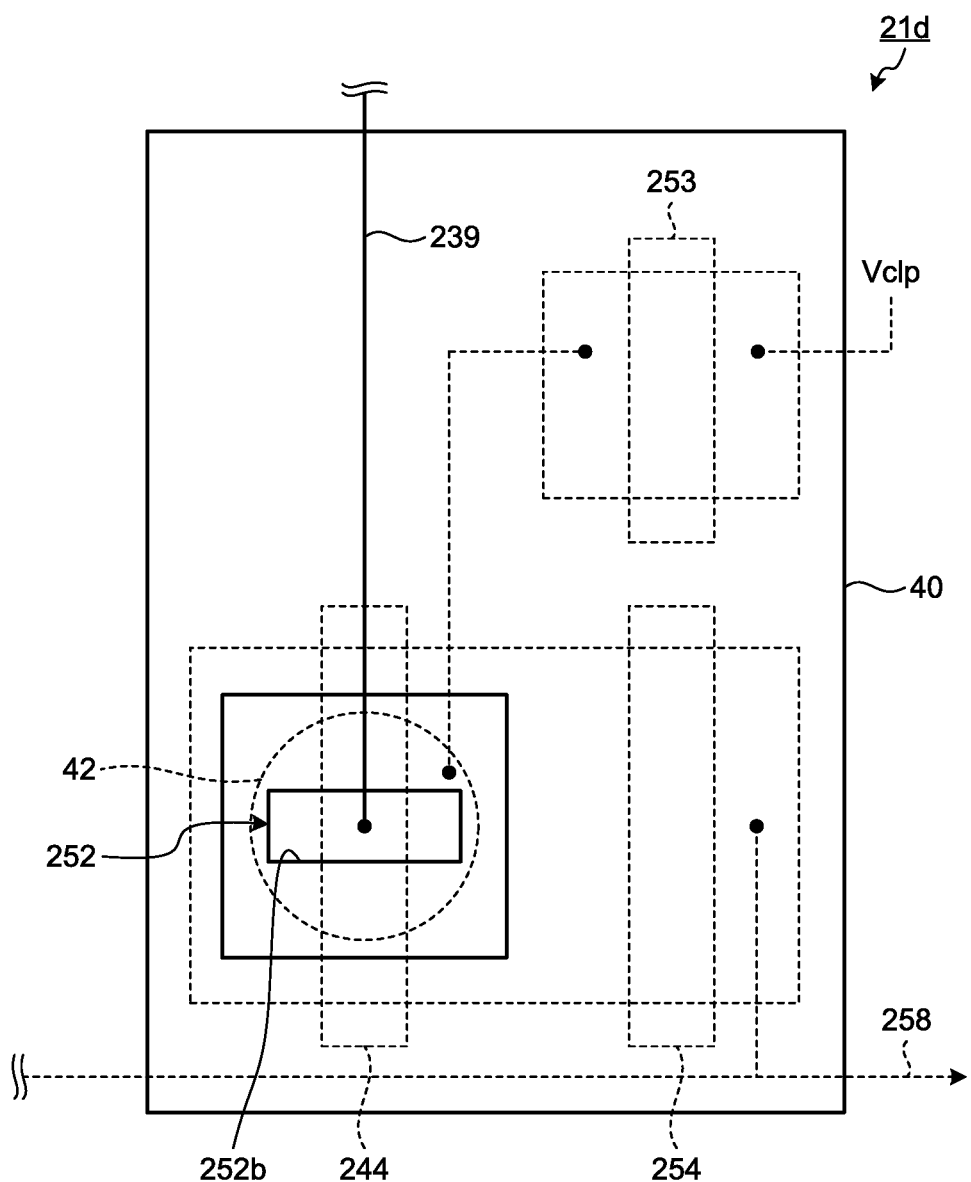
FIG. 10 is a top view including a column source follower transistor, a transfer capacity, a clamp switch, and a column selection switch of a first chip according to a second embodiment of the disclosure.
Figure 11:
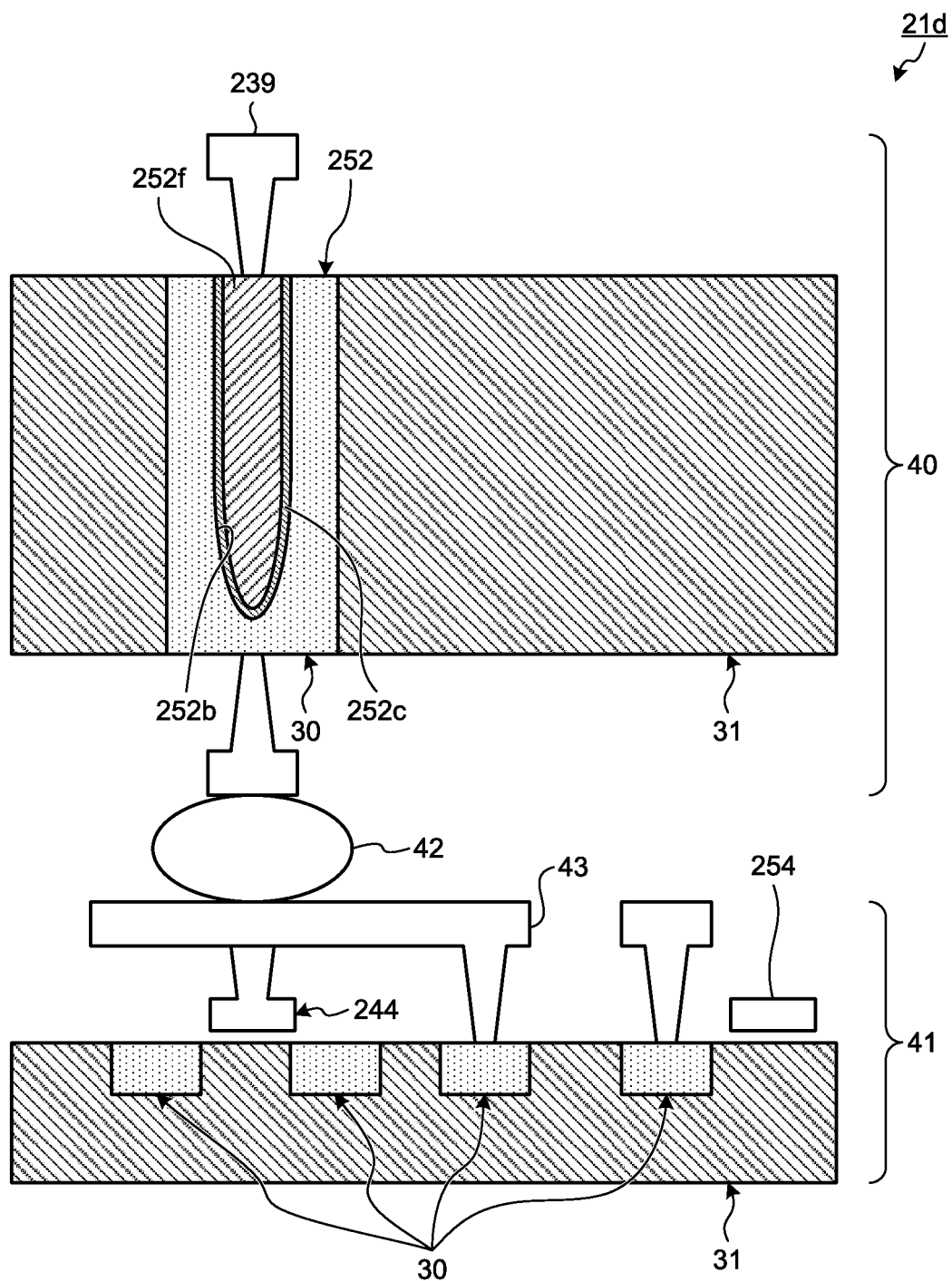
FIG. 11 is a cross-sectional view obtained by cutting a first chip at a position including a transfer capacity according to the second embodiment of the disclosure.

FIG. 10 is a top view including a column source follower transistor, a transfer capacity, a clamp switch, and a column selection switch of a first chip according to the second embodiment of the disclosure. FIG. 11 is a cross-sectional view obtained by cutting the first chip at a position including the transfer capacity according to the second embodiment of the disclosure. Additionally, the configurations of the unit pixel 230 and the like are omitted in FIGS. 10 and 11 in order to simplify the description.

A first chip 21d illustrated in FIGS. 10 and 11 is configured by using a front side illumination imager chip. The first chip 21d includes a pixel chip 40, a circuit chip 41, a connection portion 42 (a bump) which electrically connects the pixel chip 40 and the circuit chip 41 to each other, and a first electrode 43 which is provided between the connection portion 42 and the circuit chip 41. The first chip 21d is formed by sequentially stacking the circuit chip 41, the first electrode 43, the connection portion 42, and the pixel chip 40.

The circuit chip 41 is provided with the column source follower transistor 244, the clamp switch 253, and the column selection switch 254.

The first electrode 43 is provided to be stacked on the column source follower transistor 244, a lower end thereof is connected to the column source follower transistor 244, and an upper end thereof is connected to the connection portion.

The connection portion 42 is provided to be stacked on the first electrode 43, a lower end thereof is connected to the first electrode 43, and an upper end thereof is connected to the pixel chip 40. The connection portion 42 is formed by using, for example, gold or the like.

The pixel chip 40 is provided with the vertical transfer line 239 and the transfer capacity 252. Additionally, the pixel chip 40 is provided with the unit pixel 230 (not illustrated). The transfer capacity 252 includes the trench 252b which is formed in the first diffusion layer 30, the dielectric film 252c which is formed inside the trench 252b, an electrode 252f which is formed inside the dielectric film 252c, and the second diffusion layer 31 which separates the first diffusion layer 30. Further, the first diffusion layer 30 is connected to the vertical transfer line 239.

According to the above-described second embodiment of the disclosure, since circuits such as the column source follower transistor 244, the clamp switch 253, and the column selection switch 254 are disposed on the circuit chip 41 different from the pixel chip 40, it is possible to realize further miniaturization compared to the above-described first embodiment.

Additionally, in the second embodiment of the disclosure, a plurality of transfer capacities may be provided inside the pixel chip. Accordingly, it is possible to obtain the imaging signal with higher image quality.

Third Embodiment

Next, a third embodiment of the disclosure will be described. In the third embodiment, a back side illumination imager chip will be used as the first chip. For this reason, a configuration of the first chip according to the third embodiment will be described here below. In addition, the same reference numerals will be given to the same elements as those of the endoscope system 1 according to the above-described first embodiment and the description thereof will be omitted.

Figure 12:
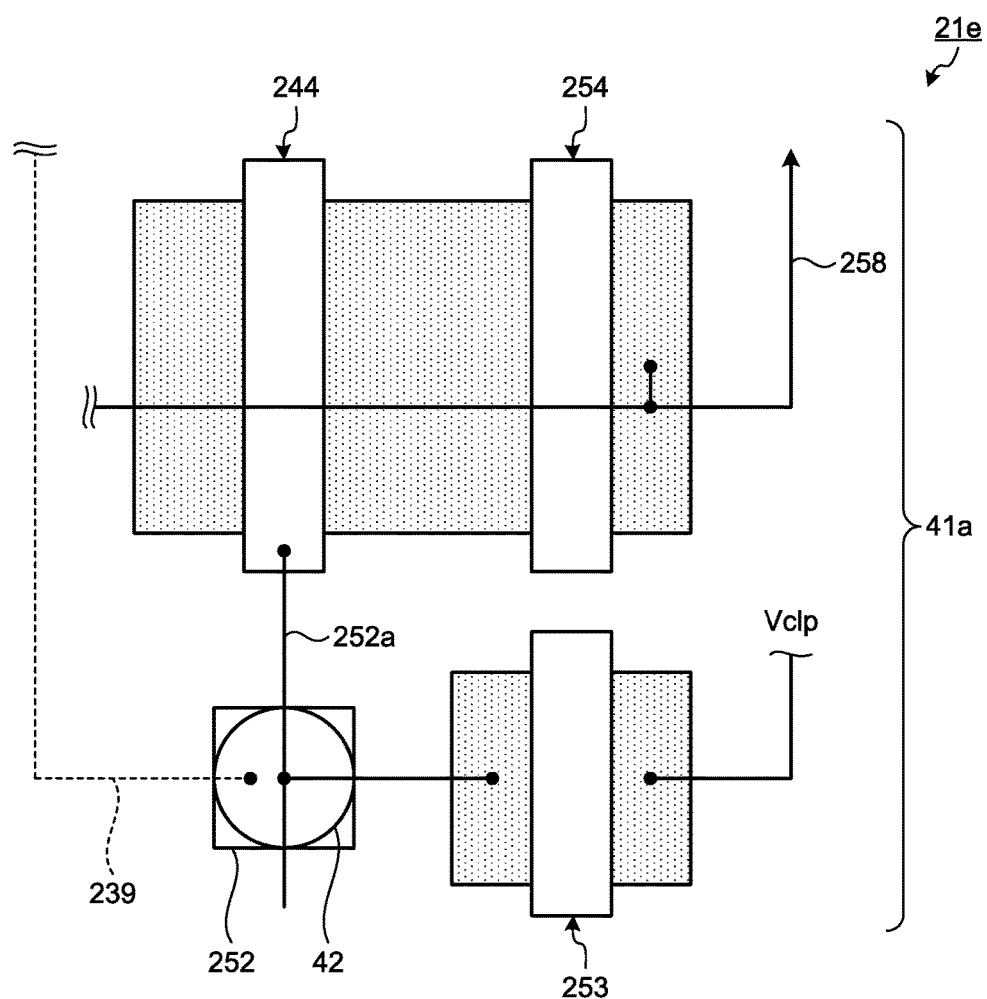
FIG. 12 is a top view of a circuit chip in a first chip according to a third embodiment of the disclosure.
Figure 13:
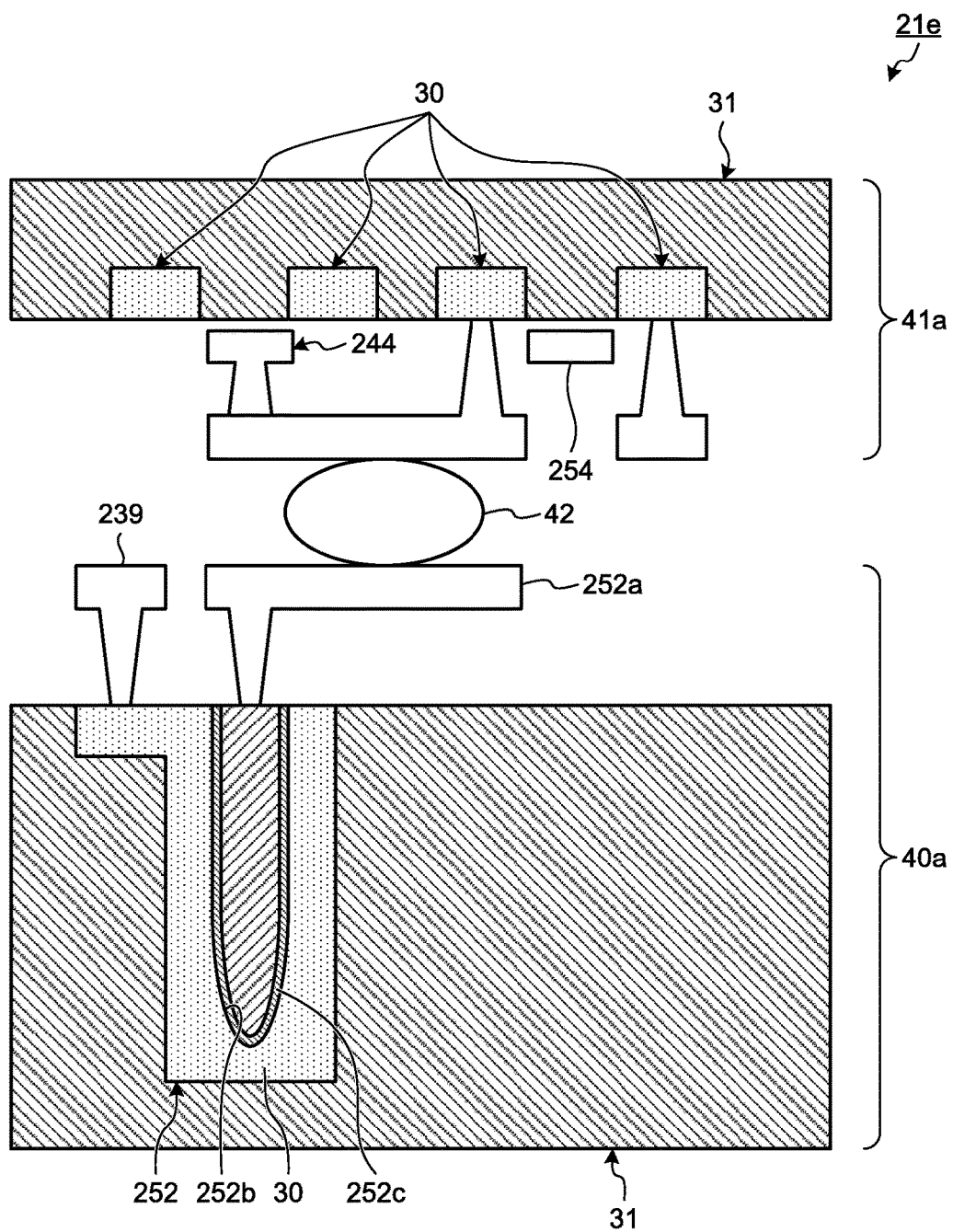
FIG. 13 is a cross-sectional view obtained by cutting at a position including a transfer capacity in the first chip according to the third embodiment of the disclosure.

FIG. 12 is a top view of a circuit chip of a first chip according to the third embodiment of the disclosure. FIG. 13 is a cross-sectional view obtained by cutting at a position including the transfer capacity of the first chip according to the third embodiment of the disclosure. In addition, the configurations of the unit pixel 230 and the like are omitted in order to simplify the description in FIGS. 12 and 13.

A first chip 21e illustrated in FIGS. 12 and 13 is configured by using a back side illumination imager chip. The first chip 21e includes a pixel chip 40a, a circuit chip 41a, and a connection portion 42 (a bump) which electrically connects the pixel chip 40a and the circuit chip 41a to each other. The first chip 21e is formed by sequentially stacking the pixel chip 40a, the connection portion 42, and the circuit chip 41a.

The pixel chip 40a is provided with the vertical transfer line 239 and the transfer capacity 252. In addition, the pixel chip 40a is provided with the unit pixel 230 (not illustrated). The transfer capacity 252 includes the trench 252b which is formed in the first diffusion layer 30, the dielectric film 252c which is formed inside the trench 252b, the first electrode 252a which is formed inside the dielectric film, and the second diffusion layer 31 which separates the first diffusion layer 30. Further, the first diffusion layer 30 is connected to the vertical transfer line 239.

The connection portion 42 is provided to be stacked on the first electrode 252a, a lower end thereof is connected to the first electrode 252a, and an upper end thereof is connected to the circuit chip 41a. The connection portion 42 is formed by using, for example, gold or the like.

The circuit chip 41a is provided with the column source follower transistor 244, the clamp switch 253, and the column selection switch 254.

According to the above-described third embodiment of the disclosure, since circuits such as the column source follower transistor 244, the clamp switch 253, and the column selection switch 254 are disposed on the circuit chip 41a different from the pixel chip 40a, it is possible to realize further miniaturization compared to the above-described first embodiment.

According to some embodiments, it is possible to realize compatibility between further miniaturization and high image quality.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image sensor comprising:
a pixel chip provided with a plurality of pixels, a plurality of first transfer lines, and a plurality of capacitors,
the pixels being arranged in a two-dimensional matrix shape, each pixel being configured to receive external light, generate an imaging signal in response to a light receiving amount and output the generated imaging signal,
the first transfer lines being configured to transfer the imaging signal output from each of the pixels, each first transfer line being provided for each vertical line in an arrangement of the pixels,
each capacitor being provided at a respective one of the first transfer lines and having a trench structure including: a first diffusion layer connected to the first transfer line; a trench formed in the first diffusion layer; a dielectric film formed inside the trench; and an electrode provided inside the dielectric film;
a circuit chip provided with a plurality of column reading circuits, a plurality of column scanning circuits, a second transfer line, and a constant current source,
each column reading circuit including:
a first transistor including a gate connected to the electrode, the first transistor being configured to amplify the imaging signal; and
a second transistor including a source connected to the electrode, the second transistor being configured to reset the capacitor to a predetermined potential,
each column reading circuit being provided at a respective one of the first transfer lines and separated from the capacitor by a second diffusion layer,
each column scanning circuit including a third transistor connected to the first transfer line via the capacitor and configured to output the imaging signal from the first transfer line via the first transistor, each column scanning circuit being provided at a respective one of the column reading circuits,
the second transfer line being connected to the third transistor and configured to transfer the imaging signal via the first transistor,
the constant current source being connected to the second transfer line and configured to output the imaging signal from each of the first transfer lines to the second transfer line; and
a connection portion stacked and provided between the pixel chip and the circuit chip and configured to connect the capacitor, which is arranged in the pixel chip and has the trench structure, and the first transistor arranged in the circuit chip to each other via the electrode, wherein
the capacitor is configured to form a transfer capacity removing a noise included in the imaging signal and connect the pixel chip and the circuit chip to each other via the electrode and the connection portion.

2. An image sensor comprising:
a pixel chip provided with a plurality of pixels, a plurality of first transfer lines, and a plurality of capacitors,
the pixels being arranged in a two-dimensional matrix shape, each pixel being configured to receive external light, generate an imaging signal in response to a light receiving amount and output the generated imaging signal, the first transfer lines being configured to transfer the imaging signal output from each of the pixels, each first transfer line being provided for each vertical line in an arrangement of the pixels, each capacitor being provided at a respective one of the first transfer lines and having a trench structure including: a first diffusion layer; a trench formed in the first diffusion layer; a dielectric film formed inside the trench; and an electrode provided inside the dielectric film and connected to the first transfer line;

a circuit chip provided with a plurality of column reading circuits, a plurality of column scanning circuits, a second transfer line, and a constant current source, each column reading circuit including:
   a first transistor including a gate connected to the first diffusion layer, the first transistor being configured to amplify the imaging signal; and
   a second transistor including a source connected to the first diffusion layer, the second transistor being configured to reset the capacitor to a predetermined potential, each column reading circuit being provided at a respective one of the first transfer lines and separated from the capacitor by a second diffusion layer, each column scanning circuit including a third transistor connected to the first transfer line via the capacitor and configured to output the imaging signal from the first transfer line via the first transistor, each column scanning circuit being provided at a respective one of the column reading circuits, the second transfer line being connected to the third transistor and configured to transfer the imaging signal via the first transistor, the constant current source being connected to the second transfer line and configured to output the imaging signal from each of the first transfer lines to the second transfer line; and a connection portion stacked and provided between the pixel chip and the circuit chip and configured to connect the capacitor, which is arranged in the pixel chip and has the trench structure, and the first transistor arranged in the circuit chip to each other via the first diffusion layer, wherein the capacitor is configured to form a transfer capacity removing a noise included in the imaging signal and connect the pixel chip and the circuit chip to each other via the first diffusion layer and the connection portion.

3. The image sensor according to claim 1, further comprising:

a separation member configured to separate the first diffusion layer and the second diffusion layer from each other.

4. The image sensor according to claim 2,
wherein the pixel chip is stacked on the circuit chip.

5. The image sensor according to claim 1,
wherein the circuit chip is stacked on the pixel chip.

6. The image sensor according to claim 1,
wherein the separation member is stacked on the pixel chip, and
the circuit chip is stacked on the separation member.

7. The image sensor according to claim 2,
wherein the separation member is stacked on the circuit chip, and
the pixel chip is stacked on the separation member.

* * * * *